United States Patent [19]

Ishida et al.

[11] 3,991,045
[45] Nov. 9, 1976

[54] N[4]-ACYLARABINONUCLEOSIDES

[75] Inventors: Torao Ishida; Kageyasu Akashi; Koichi Yoshida; Minoru Akiyama; Yoshio Sakurai; Shigeru Tsukagoshi, all of Tokyo, Japan

[73] Assignee: Asahi Kasei Kogyo Kabushiki Kaisha, Osaka, Japan

[22] Filed: Jan. 10, 1975

[21] Appl. No.: 540,294

Related U.S. Application Data

[63] Continuation-in-part of Ser. No. 474,633, May 30, 1974, abandoned.

[30] Foreign Application Priority Data

May 30, 1973 Japan.................................. 48-56709

[52] U.S. Cl..................................... 536/23; 424/180
[51] Int. Cl.$^2$......................................... C07H 19/06
[58] Field of Search............................. 260/211.5 R

[56] References Cited
UNITED STATES PATENTS

| | | |
|---|---|---|
| 3,309,359 | 3/1967 | Duschinsky et al.......... 260/211.5 R |
| 3,317,512 | 5/1967 | Wechter....................... 260/211.5 R |
| 3,457,253 | 7/1969 | Wechter....................... 260/211.5 R |
| 3,804,827 | 4/1974 | Robins et al................. 260/211.5 R |

OTHER PUBLICATIONS

Montgomery et al., "Jour. of Medicinal Chem.", vol. 15, No. 1, 1972, pp. 116–118.

*Primary Examiner*—Johnnie R. Brown
*Attorney, Agent, or Firm*—Sughrue, Rothwell, Mion, Zinn & Macpeak

[57] ABSTRACT

An N[4]-acyl-1-β-D-arabinofuranosylcytosine having the following formula

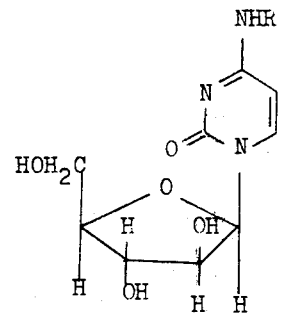

wherein R is an aliphatic acyl group having 3 to 35 carbon atoms. The compounds of this invention are useful as a cancer chemotherapeutic agent for controlling tumors, e.g., in mice, an insecticide, and a fungicidal surface active agent.

8 Claims, No Drawings

$N^4$-ACYLARABINONUCLEOSIDES

CROSS REFERENCE TO RELATED APPLICATIONS

This application is a continuation in-part application of copending application Ser. No. 474,633, filed May 30, 1974, now abandoned and claims priority to Japanese Applications 59709/73, filed May 30, 1973, and 89482/74, filed Aug. 6, 1974.

BACKGROUND OF THE INVENTION

1. FIELD OF THE INVENTION

This invention relates to $N^4$-acyl-1-$\beta$-D-arabinofuranosylcytosines having utility as a chemotherapeutic agent in controlling tumors, e.g., in mice, as an insecticide, and a fungicidal surface active agent.

2. DESCRIPTION OF THE PRIOR ART

1-$\beta$-D-Arabinofuranosylcytosine which forms the base skeleton of the compound of this invention has already been used on a practical basis as a cancer chemo-therapeutic agent, but has the defect that deamination in vivo by deaminase easily occurs with conversion to 1-$\beta$-D-arabinofuranosyluracyl, which is ineffective.

A known substance, $N^4$-acetyl-1-$\beta$-D-arabinofuranosylcytosine has an anti-cancer effect about half of that of 1-$\beta$-D-arabinofuranosylcytosine, the base skeleton [Iris Wempen et al., J. of Medical Chem., 11, 144 (1968)], and this reduction in anti-cancer effect is presumed to be due to the masking of the amino group of the pyrimidine skeleton of the base skeleton at the $N^4$-position, which gives rise to the anti-cancer effect.

SUMMARY OF THE INVENTION

It is an object of this invention to provide compounds which do not have the defects of the prior art compounds and are effective as agents to control test tumors.

Accordingly, this invention provides $N^4$-acyl-1-$\beta$-D-arabinofuranosylcytosines having the following formula

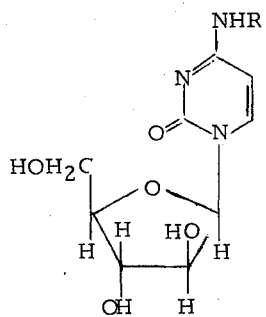

wherein R is an aliphatic acyl group having 3 to 35 carbon atoms.

DETAILED DESCRIPTION OF THE INVENTION

The compounds of this invention control test tumors in an effect equal to or greater than 1-$\beta$-D-arabinofuranosylcytosine. It was quite unexpected therefore that the compound of this invention would exhibit an anti-cancer effect equal to or greater than that of the starting material. It is not yet completely clear why the compound in accordance with this invention has an increased anti-cancer effect over the starting material while the $N^4$-acetyl derivative has a reduced anti-cancer effect as compared with the starting material. However, while not desiring to be bound one possible explanation is that the acyl group bonded to the amino group of the pyrimidine ring of the compound in accordance with the present invention undergoes a gradual hydrolysis within the living body. On the other hand, it may be that the acetyl group of $N^4$-acetyl-1-$\beta$-D-arabinofuranosylcytosine does not have suitable effects both on the deaminase action and the lipid-affinity.

As the results of further investigations, it has now also been discovered that the $N^4$-acyl-1-$\beta$-D-arabinofuranosylcytosines derived from higher fatty acids having an odd number of carbon atoms of 9 to 35 carbon atoms, which are not present in nature, exhibit an antitumor activity the same as or higher than that of 1-$\beta$-D-arabinofuranosylcytosine and further as an especially preferred embodiment of these $N^4$-acyl-1-$\beta$-D-arabinofuranosylcytosines, the $N^4$-margaroyl-1-$\beta$-D-arabinofuranosylcytosine derived from margaric acid having 17 carbon atoms is quite superior in antitumor activity to any of the $N^4$-acyl-1-$\beta$-D-arabinofuranosylcytosines derived from natural fatty acids having an even number of carbon atoms.

One known method for synthesizing $N^4$-acetyl-1-$\beta$-D-arabinofuranosylcytosine involves dissolving 1-$\beta$-D-arabinofuranosylcytosine in methanol and adding an excess of acetic anhydride many times during the reaction (Iris Wempen et al., supra). Since too much acetic anhydride is wasted in this method, this method is not commercially feasible, and is not used in the present invention.

It has now been found that the compound of this invention can be obtained almost quantitatively using a process which comprises reacting a mixture of 1-$\beta$-D-arabinofuranosylcytosine and an anhydride of a fatty acid containing at least 3 carbon atoms in a mixed solvent of a large excess of water and a watermiscible organic solvent other than an alcohol thereby to synthesize the $N^4$-acyl-1-$\beta$-D-arabinofuranosylcytosine of this invention.

In order to acylate selectively only the amino group of the arabinonucleoside in good yield, the proportions of the arabinonucleoside, the fatty acid anhydride and water must be maintained within specific ranges. In other words, the amount of the fatty acid anhydride is present in at least an equimolar proportion to the arabinonucleoside, preferably 2 to 3 molar times the proportion of the arabinonucleoside. Water is present in an at least equimolar proportion to the fatty acid anhydride, preferably in a large excess (e.g., 20 to 100 molar equivalents). In addition to this, an organic solvent miscible with water, such as dioxane, acetonitrile, acetone, tetrahydrofuran, dimethylformamide or dimethyl sulfoxide, is added until the reaction system becomes homogeneous. The amount of the organic solvent used increases depending on the number of carbon atoms of the fatty acid anhydride, but if the organic solvent is added in too large an amount, the arabinonucleoside precipitates. In such a case, the arabinonucleoside is dissolved by heating.

The fatty acid anhydride is a source of the acyl group. Only one acyl group of the anhydride reacts with the amino group of the arabinonucleoside which is N-acylated, and the other acyl group in the anhydride remains in the free state as a carboxylic acid. Water serves to prevent the hydroxyl group of the arabinofuranosyl group of the arabinonucleoside from being acylated. When an excess of the acid anhydride is present after the amino group of the arabinonucleoside has been completely acylated, the excess acid anhydride reacts with the water co-present therein, in preferance to the hydroxyl group of the arabinofuranosyl group, and is converted to a carboxylic acid.

From the standpoint of the ease of handling, dioxane is especially preferred as the solvent added to render the reaction system homogeneous. The reaction temperature can range from about 0° C to the boiling point of the solvent used, with from about room temperature (e.g., about 20° to 30° C) to 80° C being preferred. When a solvent having a boiling point of lower than 80° C is used, the reaction can be carried out at that boiling point under refluxing. The reaction time required is generally about 24 to 48 hours at room temperature, and about 3 to 5 hours at 70° to 80° C.

Since the arabinonucleoside and the N-acylarabinonucleoside have different solubilities in a solvent, the end point of the reaction can be detected by developing a part of the reaction product using thin-layer chromatography and irradiating with ultraviolet light (2537 A). After the reaction, the reaction mixture is concentrated at reduced pressure and the solvent is distilled off. A solvent in which the product is difficult to dissolve (for example, water) is added to the residue to precipitate the product. The precipitate is collected by filtration, and washed with water. ammonia, or benzene, etc. in order to remove the unreacted arabinonucleoside, the unreacted acid anhydride, and the carboxylic acid or ester formed in the reaction.

If desired, a large amount of a non-polar solvent such as n-hexane, petroleum ether, benzene or diethyl ether, can be added to the residue after concentration of the reaction mixture under reduced pressure, and the mixture can be heated under reflux, cooled, and filtered to remove the unreacted acid anhydride and the carboxylic acid formed by the reaction. The crude acylarabinonucleoside so obtained is dissolved in a suitable organic solvent such as an alcohol, for example, hot ethanol, and if desired, water is added, after which the mixture is cooled to obtain crystals of the N-acylarabinonucleoside.

Examples of suitable fatty acid anhydrides which can be used in this invention are anhydrides of saturated or unsaturated monocarboxylic acids such as propionic acid, butyric acid, isobutyric acid, valeric acid, isovaleric acid, methylethylacetic acid, pivalic acid, caproic acid, heptanoic acid, capric acid, caprylic acid, lauric acid, myristic acid, palmitic acid, stearic acid, arachidic acid, behenic acid, lignoceric acid, palmitoleic acid, oleic acid, elaidic acid, vaccenic acid, linoleic acid, linolenic acid, arachidonic acid, undecylenic acid, nonanoic acid, undecanoic acid, tridecanoic acid, pentadecanoic acid, margaric acid, nonadecanoic acid, heneicosanic acid, tricosanic acid, pentacosanic acid, heptacosanic acid, nonacosanic acid, hentriacontanic acid, ceroplastic acid, and the like or anhydrides of saturated or unsaturated dicarboxylic acids such as succinic acid, or glutaric acid.

The reaction product is identified as $N^4$-acyl-1-$\beta$-D-arabinofuranosylcytosine using elemental analysis, ultraviolet absorption spectral analysis and infrared absorption spectral analysis.

The elemental analysis values show that one acyl group has been introduced into the arabinonucleoside. It can be seen from the marked change in the ultraviolet absorption spectrum that the acyl group has been introduced into the base portion of the arabinonucleoside and not into the sugar portion. Furthermore, in the infrared absorption spectrum, the methylene and methyl absorptions due to the acyl group and amide absorption, not present in the starting substance, appear, and the absorption of $\gamma$CH becomes greater with an increasing number of carbon atoms in the fatty acid anhydride. Furthermore, the infrared absorption spectrum does not contain an ester absorption at around 1735 $cm^{-1}$. From all this, it is clear that the $N^4$-position of the base portion of the arabinonucleoside is acylated, and the hydroxyl group of the arabinose portion is not.

The following Examples are given to illustrate the present invention in greater detail. Unless otherwise indicated, all parts, percents, ratios and the like are by weight.

EXAMPLE 1

300 mg (1.23 m-mols) of 1-$\beta$-D-arabinofuranosylcytosine (molecular weight 243) was dissolved in 1.6 ml of water, and 5 ml of dioxane (molecular weight 88) was added, followed by a further addition of 415 mg (2.63 m-mols) of butyric anhydride (molecular weight 158). The mixture was stirred at room temperature for 48 hours. The reaction mixture was concentrated at reduced pressure at 60° C to obtain a solid residue. The residue was dried in a vacuum desiccator to obtain a colorless transparent jelly-like substance. Addition of 2 ml of cold water to the substance resulted in the precipitation of crystals. The crystals were rubbed well with a spoon, filtered, and thoroughly washed with cold water to form crystals. The crystals were recrystallized from a mixed solvent of water and ethanol in a volume ratio of 2:1 to form 357 mg (1.14 m-mols, yield 92.7%) of $N^4$-butyryl-1-$\beta$-D-arabinofuranosylcytosine (molecular weight 313) having a melting point of 108° to 110° C.

Elemental analysis values

Calculated (%): C, 49.83; H, 6.11; N, 13.41. Found (%): C, 49.95; H, 6.19; N, 13.40.

Ultraviolet absorption spectrum $\lambda_{max}^{H_2O}$ 298, 248, 216 m$\mu$ ($\lambda_{max}^{H_2O}$ of the starting arabinofuranosylcytosine is 272 m$\mu$)

Infrared absorption spectrum 2920 and 2865 ($\gamma$CH of $CH_3$ and $CH_2$) 1720 and 1635 ($\gamma$C= of amide —NHCO— and ureide=N-CO-N<)

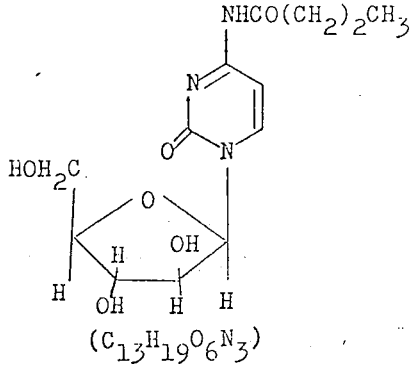

EXAMPLE 2

In the same way as described in Example 1, the following compounds were prepared from the corresponding fatty acid anhydrides.

1. $N^4$-Propionyl-1-$\beta$-D-arabinofuranosylcytosine Yield: 92.4%
Elemental analysis values for $C_{12}H_{17}O_6N_3$: Calculated (%): C, 48.16; H, 5.73; N, 14.04. Found (%): C, 48.42; H, 5.91; N, 13.95.
Ultraviolet maximum absorption at 298, 248 and 216 m$\mu$ 2. $N^4$-Isobutyryl-1-$\beta$-D-arabinofuranosylcytosine Yield: 93.1%
Elemental analysis values for $C_{13}H_{19}O_6N_3$: Calculated (%): C, 49.83; H, 6.11; N, 13.41. Found (%): C, 50.01; H, 6.24; N, 13.29.
Ultraviolet maximum absorption at 298, 248 and 216 m$\mu$ 3. $N^4$-Valeryl-1-$\beta$-D-arabinofuranosylcytosine Yield: 90.4%; Melting point: 132° to 135° C
Elemental analysis values for $C_{14}H_{21}O_6N_3$: Calculated (%): C, 51.37; H, 6.47; N, 12.84. Found (%): C, 51.55; H, 6.42; N, 12.95.
Ultraviolet maximum absorption at 298, 248 and 216 m$\mu$ 4. $N^4$-Isovaleryl-1-$\beta$-D-arabinofuranosylcytosine Yield: 92.4%
Elemental analysis values for $C_{14}H_{21}O_6N_3$: Calculated (%): C, 51.37; H, 6.47; N, 12.84. Found (%): C, 51.50; H, 6.51; N, 12.79.
Ultraviolet maximum absorption at 298, 248 and 216 m$\mu$ 5. $N^4$-Methylethylacetyl-1-$\beta$-D-arabinofuranosylcytosine Yield: 91.3%
Elemental analysis values for $C_{14}H_{21}O_6N_3$: Calculated (%): C, 51.37; H, 6.47; N, 12.84. Found (%): C, 51.42; H 6.49; N 12.92.
Ultraviolet maximum absorption at 298, 248 and 216 m$\mu$ 6. $N^4$-Pivalyl-1-$\beta$-D-arabinofuranosylcytosine Yield: 93.4%
Elemental analysis values for $C_{14}H_{21}O_6N_3$: Calculated (%): C, 51.37; H, 6.47; N, 12.84. Found (%): C, 51.25; H, 6.35; N, 12.89.
Ultraviolet maximum absorption at 298, 248 and 216 m$\mu$ 7. $N^4$-Caproyl-1-$\beta$-D-arabinofuranosylcytosine Yield: 91.2%; Melting point: 131° to 136° C
Elemental analysis values for $C_{15}H_{23}O_6N_3$:
Calculated (%): C, 52.77, H, 6.79, N, 12.31. Found (%): C, 52.73, H, 6.72, N, 12.35.
Ultraviolet maximum absorption at 299, 248 and 216 m$\mu$ 8. $N^4$-Succinyl-1-$\beta$-D-arabinofuranosylcytosine Yield: 90.8%
Elemental analysis values for $C_{13}H_{17}O_8N_3$. Calculated (%): C, 45.40; H, 4.99; N, 12.24. Found (%): C, 45.39; H, 4.99; N, 12.13.
Ultraviolet maximum absorption at 299, 248 and 216 m$\mu$ 9. $N^4$-Glutaryl-1-$\beta$-D-arabinofuranosylcytosine Yield: 90.3%
Elemental analysis values for $C_{14}H_{18}O_8N_3$;
Calculated (%): C, 47.06; H, 5.36; N, 11.76. Found (%): C, 46.92; H, 5.31; N, 11.71.
Ultraviolet maximum absorption at 299, 248 and 216 m$\mu$ In the preparations for $N^4$-succinyl-1-$\beta$-D-arabinofuranosylcytosine and $N^4$-glutaryl-1-$\beta$-D-arabinofuranosylcytosine, the following post-treatment was suitable. That is, after completion of the reaction, the reaction solution was concentrated at reduced pressure at 60° C to obtain a solid residue. 10 ml of diethyl ether was then added to the residue and the mixture was thoroughly shaken, followed by decantation. This ether-treatment was repeated 3 times. The resulting residue was dried in a vacuum desiccator to obtain a colorless transparent jelly-like substance. The substance thus obtained was recrystallized from a mixed solvent of acetone and isopropanol.

EXAMPLE 3

300 mg (1.23 m-mols) of 1-$\beta$-D-arabinofuranosylcytosine (molecular weight 243) was dissolved in 2 ml of water, and 12 ml of dioxane (molecular weight 88) was added, followed by a further addition of 6.67 mg (2.47 m-mols) of caprylic anhydride (molecular weight 270). The mixture was stirred at room temperature for 48 hours. The reaction mixture was concentrated at 60° C at reduced pressure to form a solid residue. The residue was dried in a vacuum desiccator to form a colorless substance. 20 ml of n-hexane was added, and the mixture was heated under reflux, and cooled, followed by filtration to remove the resulting oily material together with the n-hexane. Addition of 2 ml of water to the material resulted in the formation of a precipitate. After thorough rubbing with a spoon, the precipitate was filtered, and washed well with water, then with 0.1N aqueous ammonia and again with water. The precipitate was recrystallized from a mixed solvent of water and ethanol in a volume ratio of 1:1 to obtain 443 mg (1.20 m-mols, yield 97.5%) of $N^4$-caprylyl-1-$\beta$-D-arabinofuranosylcytosine (molecular weight 369) having a melting point of 151° to 153° C.

Elemental analysis values

Calculated (%): C, 55.3; H, 7.3; N, 11.4. Found (%): C, 55.2; H, 7.2; N, 11.2.

Ultraviolet absorption spectrum $\lambda_{max}$ $H_2O$ 299, 247, 214 m$\mu$

Infrared absorption spectrum 2910 and 2845 ($\gamma$CH of $CH_2$ and $CH_3$)
1710 and 1635 ($\gamma$C=O of ureide and amide)

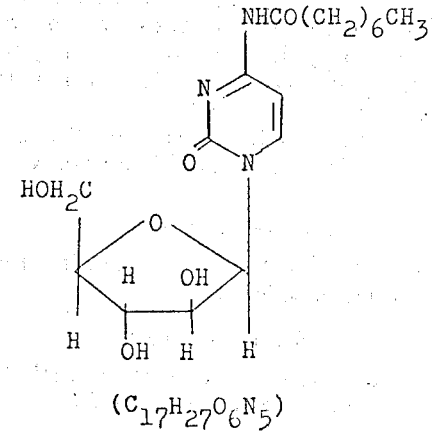

EXAMPLE 4

In the same way as described in Example 3, the following products were prepared by reacting the corresponding 1-β-D-arabinofuranosylcytosines and fatty acid anhydrides.

1. $N^4$-Heptanoyl-1-β-D-arabinofuranosylcytosine Yield: 91.3%; Melting point: 131° to 136° C Elemental analysis values for $C_{16}H_{25}O_6N_3$: Calculated (%): C, 54.07; H, 7.09; N, 11.83. Found (%): C, 54.01; H, 7.02; N, 11.89.

Ultraviolet maximum absorption at 299, 247 and 214 mμ

2. $N^4$-Capryl-1-β-D-arabinofuranosylcytosine Yield: 92.3% Melting point: 148° to 151° C Elemental analysis values for $C_{19}H_{31}O_6N_3$: Calculated (%): C, 57.41; H, 7.86; N, 10.57. Found (%): C, 57.39; H, 7.89; N, 10.51.

Ultraviolet maximum absorption at 299, 247 and 214 mμ

3. $N^4$-Lauroyl-1-β-D-arabinofuranosylcytosine Yield: 91.5% Melting point: 146° to 149° C Elemental analysis values for $C_{21}H_{35}O_6N_3$: Calculated (%): C, 59.27, H, 8.29, N, 9.88 Found (%): C, 59.26, H, 8.25, N, 9.91

Ultraviolet maximum absorption at 299, 247 and 214 mμ

4. $N^4$-Myristoyl-1-β-D-arabinofuranosylcytosine Yield: 90.5%

Melting point: 143° to 146° C

Elemental analysis values for $C_{33}H_{39}O_6N_3$ Calculated (%): C, 60.90; H, 8.67; N, 9.27. Found (%): C, 60.92; H, 8.66; N, 9.25.

Ultraviolet maximum absorption at 299, 247 and 214 mμ

EXAMPLE 5

300 ml (1.23 m-mols) of 1-β-D-arabinofuranosylcytosine (molecular weight 245) was dissolved in 2 ml of water, and 30 ml of dioxane (molecular weight 88) and 1.36 g (2.47 m-mols) of stearic anhydride (molecular weight 551) were added. The mixture was heated to 80° C to dissolve the precipitate. After stirring for 5 hours at 80° C, the reaction mixture was allowed to cool, and the resulting precipitate was collected by filtration. The precipitate was then fully washed with water, dried in a vacuum dessicator, and then heated under reflux with 30 ml of n-hexane for 30 minutes. The mixture was cooled, and collected by filtration. This treatment with n-hexane was repeated three times. The white solid thus obtained was dissolved in ethyl acetate and recrystallized from this solvent to form 566 mg (1.11 m-mols, yield 90.3%) of $N^4$-stearoyl-1-β-D-arabinofuranosylcytosine (molecular weight 510) having a melting point of 147° to 151° C.

Elemental analysis values Calculated (%): C, 63.6; H, 9.2; N, 8.4. Found (%): C, 63.7; H, 9.3; N, 8.1.s Ultraviolet absorption $\lambda_{max}^{CH_3OH}$ 300, 248, 215 mμ (measured in methanol because was insoluble in water)

Infrared absorption 2915 and 2845 (absorption of $CH_2$ and $CH_3$) 1705 and 1635 (absorption of ureide and amide)

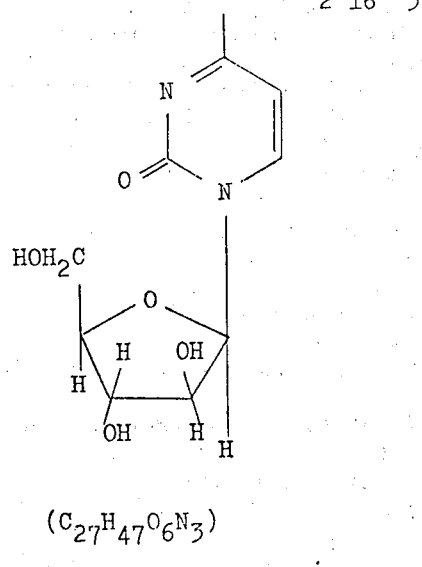

($C_{27}H_{47}O_6N_3$)

EXAMPLE 6

In the same way as described in Example 5, the following products were prepared from the corresponding 1-β-D-arabinofuranosylcytosines and fatty acid anhydrides.

1. $N^4$-Palmitoyl-1-β-D-arabinofuranosylcytosine Yield: 92.3% Melting point: 139° to 143° C.

Elemental analysis values for $C_{25}H_{43}O_6N_3$: Calculated (%): C, 62.34; H, 9.00; N, 8.73. Found (%): C, 62.39; H, 9.02; N, 8.71.

Ultraviolet maximum absorption at 300, 248 and 215 mμ

2. $N^4$-Arachidoyl-1-β-D-arabinofuranosylcytosine Yield: 91.5%; Melting point: 138° to 142° C Elemental analysis values of $C_{29}H_{51}O_6N_3$: Calculated (%): C, 64.77; H, 9.56; N, 7.82. Found (%): C, 64.75; H, 9.57; N, 7.89.

Ultraviolet maximum absorption at 300, 248 and 215 mμ

3. $N^4$-Behenoyl-1-β-D-arabinofuranosylcytosine Yield: 92.4%; Melting point: 141° to 143° C Elemental analysis values for $C_{31}H_{55}O_6N_3$: Calculated (%): C, 65.81; H, 9.80; N, 7.43. Found (%): C, 65.79; H, 9.82; N, 7.41.

Ultraviolet maximum absorption at 300, 248 and 215 mμ

4. $N^4$-Palmitoleoyl-1-β-D-arabinofuranosylcytosine Yield: 91.3%

Elemental analysis values for $C_{25}H_{41}O_6N_3$: Calculated (%): C, 62.60; H, 8.62; N, 8.76. Found (%): C, 62.65; H, 8.64; N, 8.77.

Ultraviolet maximum absorption at 300, 248 and 215 mμ

5. N⁴-Oleoyl-1-β-D-arabinofuranosylcytosine Yield: 91.1% Melting point: 132° to 137° C Elemental analysis values for $C_{27}H_{45}O_6N_3$: Calculated (%): C, 63.88; H, 8.94; N, 8.28. Found (%): C, 63.85; H, 8.97; N, 8.31.

Ultraviolet maximum absorption at 300, 248 and 215 mμ

6. N⁴-Elaidoyl-1-β-D-arabinofuranosylcytosine Yield: 89.7%

Elemental analysis values of $C_{27}H_{45}O_6N_3$: Calculated (%): C, 63.88; H, 8.94; N, 8.28. Found (%): C, 63.86; H, 8.94; N, 8.29.

Ultraviolet maximum absorption at 300, 248 and 215 mμ

7. N⁴-Vaccenoyl-1-β-D-arabinofuranosylcytosine Yield: 91.5%

Elemental analysis values for $C_{27}H_{45}O_6N_3$: Calculated (%): C, 63.88; H, 8.94; N, 8.28. Found (%): C, 63.88; H, 8.96; N, 8.25.

Ultraviolet maximum absorption at 300, 248 and 215 mμ

8. N⁴-Linoleoyl-1-β-D-arabinofuranosylcytosine Yield: 91.3%

Elemental analysis values for $C_{27}H_{43}O_6N_3$: Calculated (%): C, 64.13; H, 8.57; N, 8.31. Found (%): C, 64.11; H, 8.56; N, 8.27.

Ultraviolet maximum absorption at 300, 248 and 215 mμ

9. N⁴-Linolenoyl-1-β-D-arabinofuranosylcytosine Yield: 89.9%

Elemental analysis values for $C_{27}H_{41}O_6N_3$: Calculated (%): C, 64.39; H, 8.21; N, 8.34. Found (%): C, 64.37; H, 8.20; N, 8.34.

Ultraviolet maximum absorption at 300, 248 and 215 mμ

10. N⁴-Arachidonoyl-1-β-D-arabinofuranosylcytosine Yield: 89.5%

Elemental analysis values for $C_{29}H_{43}O_6N_3$: Calculated (%): C, 65.76; H, 8.18; N, 7.93. Found (%): C, 65.73; H, 8.19; N, 7.95.

Ultraviolet maximum absorption at 300, 248 and 215 mμ

EXAMPLE 7

In 2 ml of water was dissolved 300 mg (1.23 m-mols) of 1-β-D-arabinofuranosylcytosine (molecular weight 243) and after adding to the solution 30 ml of dioxane (molecular weight 88) and 736 mg (2.47 m-mols) of nonanoic anhydride (molecular weight 298), the mixture was heated to 80° C to dissolve the solid materials. After stirring the reaction system for 5 hours at 80° C, the reaction mixture was allowed to cool and the precipitates thus formed were collected by filtration, washed sufficiently with water, and dried. The precipitates obtained were added to n-hexane followed by refluxing and after cooling, the precipitates formed were collected by filtration and recrystallized from ethyl acetate to provide 463 mg (1.21 m-moles) of N⁴-nonanoyl-1-β-D-arabinofuranosylcytosine (molecular weight 383) at a yield of 98.4% and with a melting point of 150° to 152° C.

Elemental analysis values

Calculated (%): C, 56.38; H, 7.62; N, 10.96. Found (%): C, 56.33; H, 7.61; N, 10.97.

Ultraviolet absorption spectrum (measured in methanol since the product was insoluble in water):

$\lambda_{max}^{CH_3OH}$ 299 mμ, 247 mμ, and 214 mμ

Infrared absorption spectrum:

2915 cm⁻¹ and 2845 cm⁻¹ (absorptions of CH₂ and CH₃) and 1705 cm⁻¹ and 1635 cm⁻¹ (absorptions of ureide and amide)

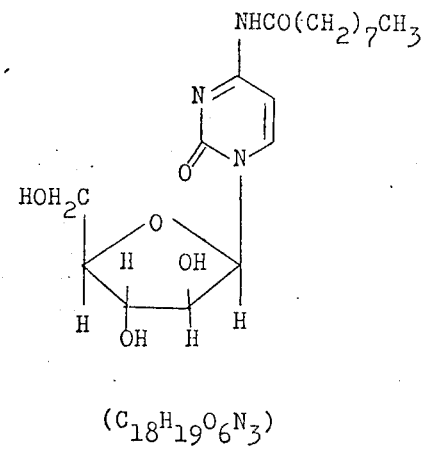

$(C_{18}H_{19}O_6N_3)$

EXAMPLE 8

In 2 ml of water was dissolved 300 mg (1.23 m-mols) of 1-β-D-arabinofuranosylcytosine (molecular weight 243) and after adding to the solution 30 ml of dioxane (molecular weight 88) and 874 mg (2.47 m-mols) of undecanoic anhydride (molecular weight 354), the mixture was heated to 80° C to dissolve the solid materials. After stirring the solution for 5 hours at 80° C, the reaction mixture was allowed to cool and the precipitates formed were collected by filtration, washed sufficiently with water, and dried. Then, the precipitates were added to n-hexane followed by refluxing and after cooling, the precipitates were collected by filtration and recrystallized from ethyl acetate to provide 497 mg (1.21 m-mols) of N⁴-undecanoyl-1-β-D-arabinofuranosylcytosine (molecular weight 411) at a yield of 98.4% with a melting point of 146° to 150° C.

Elemental analysis values

Calculated (%): C, 58.37; H, 8.08; N, 10.21. Found (%): C, 58.36; H, 8.07; N, 10.22.

Ultraviolet absorption spectrum (measured in methanol since the produce was insoluble in water):

$\lambda_{max}^{CH_3OH}$ 299 mμ, 247 mμ, and 214 mμ

Infrared absorption spectrum:

2925 cm⁻¹ and 2855 cm⁻¹ (absorptions of CH₂ and CH₃) 1695 cm⁻¹ and 1645 cm⁻¹ (absorptions of ureide and amide)

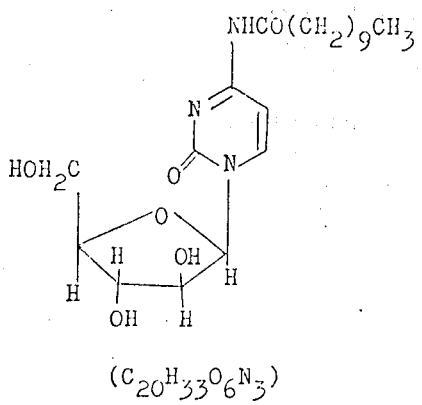

$(C_{20}H_{33}O_6N_3)$

EXAMPLE 9

In 2 ml of water was dissolved 300 mg (1.23 m-mols) of 1-β-D-arabinofuranosylcytosine (molecular weight 243) and after adding to the solution 30 ml of dioxane (molecular weight 88) and 1012 mg (2.47 m-mols) of tridecanoic anhydride (molecular weight 410), the mixture was heated to 80° C to dissolve the solid materials. After stirring the solution for 5 hours at 80° C, the reaction mixture was allowed to cool and the precipitates formed were collected by filtration, washed sufficiently with water, and dried. Then, the precipitates were added to n-hexane followed by refluxing. After cooling, the precipitates were collected by filtration and recrystallized from ethyl acetate to provide 531 mg (1.21 m-mols) of $N^4$-tridecanoyl-1-β-D-arabinofuranosylcytosine (molecular weight 439) at a yield of 98.4% with a melting point of 143° to 146° C.

Elemental analysis values Calculated (%): C, 60.11; H, 8.49; N, 9.56. Found (%): C, 60.12; H, 8.50; N, 9.56.

Ultraviolet absorption spectrum (measured in methanol since the product was insoluble in water):

$\lambda_{max}^{CH_3OH}$ 299 mμ, 247 mμ, and 214 mμ

Infrared absorption spectrum 2920 cm$^{-1}$ and 2860 cm$^{-1}$ (absorptions of $CH_2$ and $CH_3$) 1690 cm$^{-1}$ and 1640 cm$^{-1}$ (absorptions of ureide and amide)

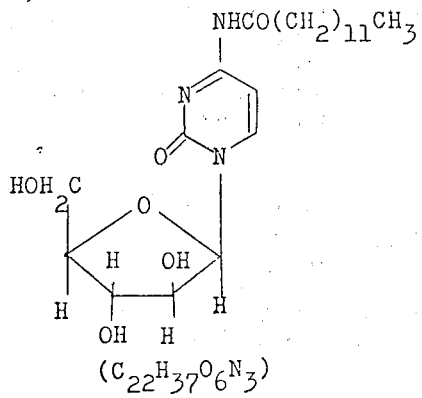

$(C_{22}H_{37}O_6N_3)$

EXAMPLE 10

In 2 ml of water was dissolved 300 mg (1.23 m-mols) of 1-β-D-arabinofuranosylcytosine (molecular weight 243) and after adding to the solution 30 ml of dioxane (molecular weight 88) and 1151 mg (2.47 m-mols) of pentadecanoic anhydride (molecular weight 466), the mixture was heated to 80° C to dissolve the solid materials. After stirring the solution for 5 hours at 80° C, the reaction mixture was allowed to cool and the precipitates formed were collected by filtration, washed sufficiently with water, and dried.

Then, the precipitates were added to n-hexane followed by refluxing and after cooling, the precipitates were collected by filtration and recrystallized from ethyl acetate to provide 565 mg (1.21 m-mols) of $N^4$-pentadecanoyl-1-β-D-arabinofuranosylcytosine (molecular weight 467) at a yield of 98.4% with a melting point of 142° to 145° C.

Elemental analysis values

Calculated (%): C, 61.64; H, 8.84; N, 8.99. Found (%): C, 61.63; H, 8.83; N, 8.98.

Ultraviolet absorption spectrum (measured in methanol since the product was insoluble in water):

$\lambda_{max}^{CH_3OH}$ 299 mμ, 247 mμ, and 214 mμ

Infrared absorption spectrum:

2925 cm$^{-1}$ and 2855 cm$^{-1}$ (absorptions of $CH_2$ and $CH_3$) 1695 cm$^{-1}$ and 1640 cm$^{-1}$ (absorptions of ureide and amide)

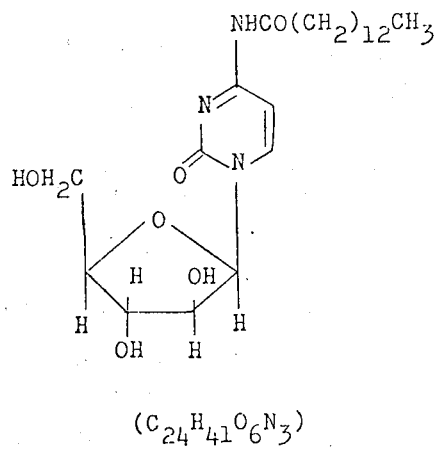

$(C_{24}H_{41}O_6N_3)$

EXAMPLE 11

To a mixture of 2 ml of water and 1289 mg (2.47 m-mols) of margaric anhydride (molecular weight 522) was added 300 mg (1.23 m-mols) of 1-β-D-arabinosylcytosine (molecular weight 243) and the mixture was heated to 80° C to dissolve the solid materials. After stirring the solution for 5 hours at 80° C, the reaction mixture was allowed to cool and the precipitates thus formed were collected by filtration, washed sufficiently with water, and dried. Then, the precipitates were added to n-hexane followed by refluxing and after cooling, the precipitates were collected by filtration and recrystallized from ethyl acetate to provide 604 mg (1.22 m-mols) of $N^4$-margaroyl-1-β-D-arabinofuranosylcytosine (molecular weight 495) at a yield of 99.2% with a melting point of 144° to 147° C.

Elemental analysis values

Calculated (%): C, 63.00; H, 9.15; N, 8.48. Found (%): C, 63.00; H, 9.14; N, 8.49.

Ultraviolet absorption spectrum (measured in methanol since the product was insoluble in water):

$\lambda_{max}^{CH_3OH}$ 299 m$\mu$, 248 m$\mu$, and 220 m$\mu$

Infrared absorption spectrum:

2930 cm$^{-1}$ and 2860 cm$^{-1}$ (absorptions of CH$_2$ and CH$_3$) 1695 cm$^{-1}$ and 1645 cm$^{-1}$ (absorptions of ureide and amide)

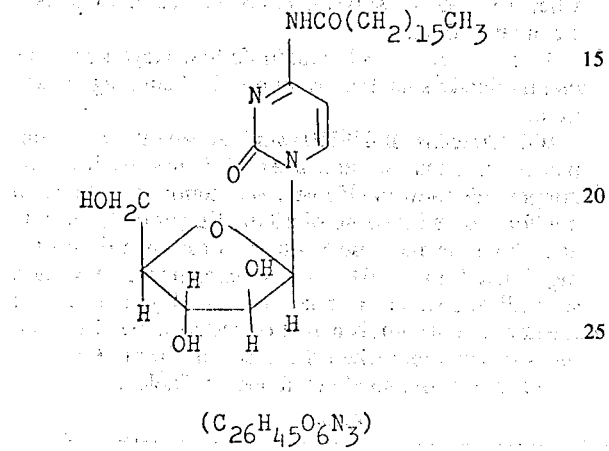

($C_{26}H_{45}O_6N_3$)

EXAMPLE 12

In 2 ml of water was dissolved 300 mg (1.25 m-mols) of 1-$\beta$-D-arabinofuranosylcytosine (molecular weight 243) and after adding to the solution 30 ml of dioxane (molecular weight 88) and 1427 mg (2.47 m-mols) of nonadecanoic anhydride (molecular weight 578), the mixture was heated to 80° C to dissolve the solid materials. After stirring the solution for 5 hours at 80° C, the reaction mixture was allowed to cool and the precipitates formed were recovered by filtration, washed sufficiently with water, and dried. Then the precipitates were added to n-hexane followed by refluxing. After cooling, the precipitates were collected by filtration and recrystallized from ethyl acetate to provide 638 mg (1.22 m-mols) of N$^4$-nonadecanoyl-1-$\beta$-D-arabinofuranosylcytosine (molecular weight 523) at a yield of 99.2% with a melting point of 139° to 142° C.

Elemental analysis values

Calculated (%): C, 64.21; H, 9.43; N, 8.02. Found (%): C, 64.20; H, 9.44; N, 8.03.

Ultraviolet absorption spectrum (measured in methanol since the product was insoluble in water):

$\lambda_{max}^{CH_3OH}$ 299 m$\mu$, 247 m$\mu$, and 215 m$\mu$

Infrared absorption spectrum:

2930 cm$^{-1}$ and 2860 cm$^{-1}$ (absorptions of CH$_2$ and CH$_3$) 1695 cm$^{-1}$ and 1642 cm$^{-1}$ (absorptions of ureide and amide)

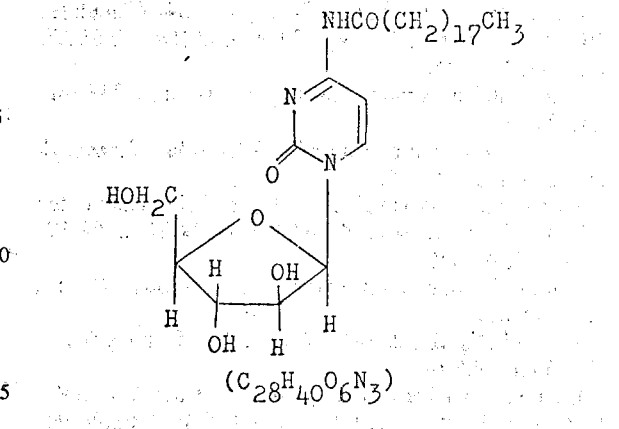

($C_{28}H_{40}O_6N_3$)

EXAMPLE 13

In 2 ml of water was dissolved 300 mg (1.23 m-mols) of 1-$\beta$-D-arabinofuranosylcytosine (molecular weight 243) and after adding to the solution 30 ml of dioxane (molecular weight 88) and 1566 mg (2.47 m-mols) of heneicosanoic anhydride (molecular weight 634), the mixture was heated to 80° C to dissolve the solid materials. After stirring the solution for 5 hours at 80° C, the reaction mixture was allowed to cool and the precipitates formed were collected by filtration, washed sufficiently, and dried. Then, the precipitates were added to n-hexane followed by refluxing. After cooling, the precipitates were collected by filtration and recrystallized from ethyl acetate to provide 661 mg (1.20 m-mols) of N$^4$-heneicosanoyl-1-$\beta$-D-arabinofuranosylcytosine (molecular weight 551) at a yield of 97.6% with a melting point of 139° to 142° C.

Elemental analysis values

Calculated (%): C, 65.30; H, 9.68; N, 7.62. Found (%): C, 65.31; H, 9.67; N, 7.64.

Ultraviolet absorption spectrum (measured in methanol since the product was insoluble in water):

$\lambda_{max}^{CH_3OH}$ 300 m$\mu$, 248 m$\mu$, and 215 m$\mu$

Infrared absorption spectrum:

2915 cm$^{-1}$ and 2845 cm$^{-1}$ (absorptions of CH$_2$ and CH$_3$) 1705 cm$^{-1}$ and 1635 cm$^{-1}$ (absorptions of ureide and amide)

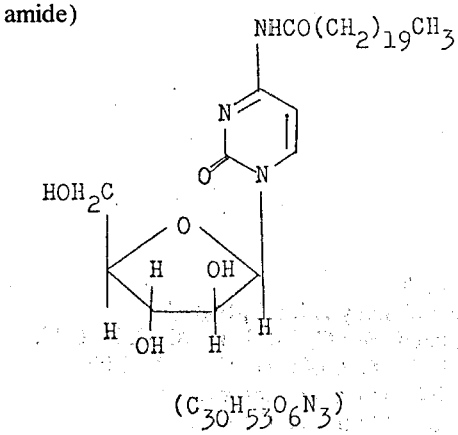

($C_{30}H_{53}O_6N_3$)

EXAMPLES 14 to 19

By following the same procedure as in Example 13, the following N$^4$-acyl-1-$\beta$-D-arabinofuranosylcytosines were produced from 1-$\beta$-D-arabinofuranosylcytosine and corresponding acid anhydrides.

14. N$^4$-n-Tricosanoyl-1-$\beta$-D-arabinofuranosylcytosine Yield: 9.18%

Elemental analysis values for $C_{32}H_{57}O_6N_3$: Calculated (%): C, 66.28; H, 9.91; N, 7.24. Found (%): C, 66.27; H, 9.92; N, 7.24.

Ultraviolet maximum absorption: 300 m$\mu$, 248 m$\mu$, and 215 m$\mu$

15. $N^4$-n-Pentacosanoyl-1-$\beta$-D-arabinofuranosylcytosine Yield: 93.4%

Elemental analysis values for $C_{34}H_{61}O_6N_3$: Calculated (%): C, 67.18; H, 10.12; N, 6.91. Found (%): C, 67.19; H, 10.12; N, 6.91.

Ultraviolet maximum absorption: 300 m$\mu$, 248 m$\mu$, and 215 m$\mu$

16. $N^4$-Heptacosanoyl-1-$\beta$-D-arabinofuranosylcytosine Yield: 92.9%

Elemental analysis for $C_{36}H_{65}O_6 N_3$: Calculated (%): C, 68.03; H, 10.23; N, 6.61. Found (%): C, 68.04; H, 10.22; N, 6.61.

Ultraviolet maximum absorption: 300 m$\mu$, 248 m$\mu$, and 215 m$\mu$

17. $N^4$-Nonacosanoyl-1-$\beta$-D-arabinofuranosylcytosine Yield: 91.7%

Elemental analysis for $C_{38}H_{69}O_6N_3$:
Calculated (%): C, 68.73; H, 10.48; N, 6.32.
Found (%): C, 68.75; H, 10.48; N, 6.33.
Ultraviolent maximum absorption:
300 m$\mu$, 248 m$\mu$, and 215 m$\mu$.

18. $N^4$-n-Hentriacontanoyl-1-$\beta$-D-arabinosylcytosine

Yield: 90.3%
Elemental analysis for $C_{40}H_{73}O_6N_3$:
Calculated (%): C, 69.42; H, 10.63; N, 6.07.
Found (%): C, 69.41; H, 10.64; N, 6.07.
Ultraviolet maximum absorption:
300 m$\mu$, 248 m$\mu$, and 215 m$\mu$ 19. $N^4$-Ceroplastoyl-1-$\beta$-D-arabinofuranosylcytosine Yield: 90.1%
Elemental analysis for $C_{44}H_{81}O_6N_3$:
Calculated (%): C, 70.68; H, 10.84; N, 5.62.
Found (%): C, 70.68; H, 10.85; N, 5.62.
Ultraviolet maximum absorption:
300 m$\mu$, 248 m$\mu$, and 215 m$\mu$

TEST EXAMPLE 1

The anti-cancer activities (in the L1210-CDF$_1$ mouse system) of the N-acylarabinonucleosides synthesized by the process of this invention were examined, and shown in terms of the rate of survival after 60 days.

Theoretically, when the rate of survival is less than 100%, the compound is toxic, when the rate of survival is 100%, there is no treatment effect; and when the rate of survival is above 100%, the compound exhibits a treatment effect. Actually, however, in view of experimental errors in animal tests, it can be judged that when the rate of survival is above 125%, there is a treatment effect.

As a control, 1-$\beta$-D-arabinofuranosylcytosine now commerically available as an anti-leukemia agent was used.

100,000 cells of L1210 were intraperitoneally implanted in a mouse, and after 25 hours, each of the compounds shown in Table 1 was administered once a day for 5 days in a dose of 50 mg/Kg (of body weight) each time (in the case of the control, in a dose of 5 mg/Kg each time). The control exhibited a maximum survival rate when the dose was 5 mg/Kg, and each of the compounds of this invention tested showed a maximum survival rate when the dose was 50 mg/Kg.

The results obtained are shown in Table 1.

Table

| | Acyl Group of the Compound Tested | Rate of Survival |
|---|---|---|
| Control | H | 170 |
| Propionyl | $CH_3CH_2CO-$ | 180 |
| Butyryl | $CH_3(CH_2)_2CO-$ | 180 |
| iso-Butyryl | $(CH_3)_2CHCO-$ | 180 |
| n-Valeryl | $CH_3(CH_2)_3CO-$ | 180 |
| iso-Valeryl | $(CH_3)_2CHCH_2CO-$ | 180 |
| Methylethylacetyl | $CH_3CH_2CH(CH_3)CO-$ | 180 |
| Pivalyl | $(CH_3)_3C-CO-$ | 180 |
| Caproyl | $CH_3(CH_2)_4CO-$ | 180 |
| Heptanoyl | $CH_3(CH_2)_5CO-$ | 190 |
| Caprylyl | $CH_3(CH_2)_6CO-$ | 200 |
| Capryl | $CH_3(CH_2)_8CO-$ | 200 |
| Lauroyl | $CH_3(CH_2)_{10}CO-$ | 200 |
| Myristoyl | $CH_3(CH_2)_{12}CO-$ | 300 |
| Palmitoyl | $CH_3(CH_2)_{14}CO-$ | 300 |
| Stearoyl | $CH_3(CH_2)_{16}CO-$ | 300 |
| Arachidoyl | $CH_3(CH_2)_{18}CO-$ | 200 |
| Behenoyl | $CH_3(CH_2)_{20}CO-$ | 200 |
| Palmitoleoyl | $CH_3(CH_2)_5-CH=CH-(CH_2)_7CO-$ (cis) | 300 |
| Oleoyl | $CH_3(CH_2)_7-CH=CH-(CH_2)_7CO-$ (cis) | 300 |
| Elaidoyl | $CH_3(CH_2)_7-CH=CH-(CH_2)_7CO-$ (trans) | 300 |
| Vaccenoyl | $CH_3(CH_2)_5-CH=CH-(CH_2)_7CO-$ | 300 |
| Linoleoyl | $CH_3(CH_2)_3(CH_2CH=CH)_2(CH_2)_7CO-$ | 300 |
| Linolenoyl | $CH_3(CH_2CH=CH)_3(CH_2)_7CO-$ | 300 |
| Arachidonoyl | $CH_3(CH_2)_3(CH_2CH=CH)_4(CH_2)_3CO-$ | 200 |
| Succinyl | $HOOC(CH_2)_2CO-$ | 180 |
| Glutaryl | $HOOC(CH_2)_3CO-$ | 180 |

It can be seen from the results obtained that when the compounds in accordance with this invention were used, the rate of survival was longer than in the case of using the control.

TEST EXAMPLE 2

A test was conducted to determine the controlling effect of the compounds of this invention on spider mites parasitic on string bean.

50% of each of the test compounds indicated in Table 2, 2 parts of a sodium alkylbenzenesulfonate (wetting agent), 3 parts of sodium dinaphthylmethanedisulfonate (dispersing agent), and 45 parts of a mixture of diatomaceous earth and kaolin were mixed and pulverized and diluted with water to prepare a wettable powder. The wettable powder was diluted with water to form a 0.1% dispersion. Larvae of spider mites inhabiting the leaves of string bean were treated in a greenhouse with this dispersion for 10 seconds, and two days later, the rate of kill was examined. The total number of spider mite larvae tested was 80.

The results obtained are shown in Table 2. As a control, p-chlorophenyl-$\beta$-chlorobenzenesulfonate was used.

ined in the following test system. The results were good and similar to those obtained in Test Example 1.

TEST SYSTEM

| | Test System |
|---|---|
| Animal | $CDF_1$ mouse, male, 3 mice/group |
| Tumor | L1210, $10^5$ cells/mouse |
| Treatment | day 2, day 6, ip |
| Sampling | saline + "Tween 80" (1 drop) |

Table 2

| | Acyl Group of the Compound Tested | Rate of Kill |
|---|---|---|
| Propionyl | $CH_3CH_2CO-$ | 100 |
| Butyryl | $CH_3(CH_2)_2CO-$ | 100 |
| iso-Butyryl | $(CH_3)_2CHCO-$ | 100 |
| n-Valeryl | $CH_3(CH_2)_3CO-$ | 100 |
| iso-Valeryl | $(CH_3)_2CHCH_2CO-$ | 100 |
| Methylethylacetyl | $CH_3CH_2CH(CH_3)CO-$ | 100 |
| Pivalyl | $(CH_3)_3C-CO-$ | 100 |
| Caproyl | $CH_3(CH_2)_4CO-$ | 100 |
| Heptanoyl | $CH_3(CH_2)_5CO-$ | 100 |
| Caprylyl | $CH_3(CH_2)_6CO-$ | 100 |
| Capryl | $CH_3(CH_2)_8CO-$ | 100 |
| Lauroyl | $CH_3(CH_2)_{10}CO-$ | 100 |
| Myristoyl | $CH_3(CH_2)_{12}CO-$ | 100 |
| Palmitoyl | $CH_3(CH_2)_{14}CO-$ | 100 |
| Stearoyl | $CH_3(CH_2)_{16}CO-$ | 100 |
| Arachidoyl | $CH_3(CH_2)_{18}CO-$ | 100 |
| Behenoyl | $CH_3(CH_2)_{20}CO-$ | 100 |
| Palmitoleoyl | $CH_3(CH_2)_5-CH=CH-(CH_2)_7CO-$ (cis) | 100 |
| Oleoyl | $CH_3(CH_2)_7-CH=CH-(CH_2)_7CO-$ (cis) | 100 |
| Elaidoyl | $CH_3(CH_2)_7-CH=CH-(CH_2)_7CO-$ (trans) | 100 |
| Vaccenoyl | $CH_3(CH_2)_5-CH=CH-(CH_2)_7CO-$ | 100 |
| Linoleoyl | $CH_3(CH_2)_3(CH_2CH=CH)_2(CH_2)_7CO-$ | 100 |
| Linolenoyl | $CH_3(CH_2CH=CH)_3(CH_2)_7CO-$ | 100 |
| Arachidonoyl | $CH_3(CH_2)_3(CH_2CH=CH)_4(CH_2)_3CO-$ | 100 |
| Succinyl | $HOOC(CH_2)_2CO-$ | 100 |
| Glutaryl | $HOOC(CH_2)_3CO-$ | 100 |
| Control | | 100 |
| Non-treated | | 0 |

TEST EXAMPLE 3

In the Chemical Therapeutic Center of Institute of Cancer Research, Japan, the cancer-controlling effect of $N^4$-acyl-1-$\beta$-D-arabinofuranosylcytosines was examined in the following test system.

Evaluation of the Test Results: dose; 400 mg/Kg, 200 mg/Kg, 100 mg/Kg

Mean Survival Time, T/C (%)

Results

| Samples | | T/C (%) Dose (mg/Kg) | | | | | |
|---|---|---|---|---|---|---|---|
| RCOO | $N^4$-RCO-Ara-C* | 400 | 200 | 100 | 75 | 50 | 25 |
| $C_4$ | $N^4$-Butyryl Ara-C | 189 | 131 | 131 | | | |
| $C_8$ | $N^4$-Caprylyl Ara-C | 163 | 127 | 123 | | | |
| $C_9$ | $N^4$-Nonanoyl Ara-C | 185 | 145 | 140 | | | |
| $C_{10}$ | $N^4$-Capryl Ara-C | 245 | 213 | 140 | | | |
| $C_{11}$ | $N^4$-Undecanoyl Ara-C | 250 | 223 | 151 | | | |
| $C_{12}$ | $N^4$-Lauroyl Ara-C | 309 | 284 | 177 | | | |
| $C_{13}$ | $N^4$-Tridecanoyl Ara-C | 302 | 301 | 253 | | | |
| $C_{14}$ | $N^4$-Myristoyl Ara-C | 90 | 127 | 206 | | | |
| $C_{15}$ | $N^4$-Pentadecanoyl Ara-C | 91 | 92 | 287 | | | |
| $C_{16}$ | $N^4$-Palmitoyl Ara-C | 92 | 92 | 292 | | | |
| $C_{17}$ | $N^4$-Margaroyl Ara-C | 99 | 188 | 397 | | | |
| $C_{18}$ | $N^4$-Stearoyl Ara-C | 111 | 121 | 273 | more than 378 | more than 272 | more than 252 |
| $C_{18}$ | $N^4$-Oleoyl Ara-C | 109 | 135 | 261 | | | |
| $C^{19}$ | $N^4$-Nonadecanoyl Ara-C | 100 | 189 | 382 | | | |
| $C_{20}$ | $N^4$-Arachidoyl Ara-C | 105 | 128 | 285 | | | |
| $C_{21}$ | $N^4$-Heneicosanoyl Ara-C | 101 | 191 | 359 | | | |
| $C_{23}$ | $N^4$-Tricosanoyl Ara-C | 99 | 189 | 342 | | | |
| $C_{25}$ | $N^4$-Pentacosanoyl Ara-C | 98 | 187 | 341 | | | |
| $C_{27}$ | $N^4$-Heptacosanoyl Ara-C | 101 | 185 | 330 | | | |
| $C_{29}$ | $N^4$-Nonacosanoyl Ara-C | 102 | 183 | 272 | | | |
| $C_{31}$ | $N^4$-Hentriacontanoyl Ara-C | 101 | 173 | 273 | | | |
| $C_{35}$ | $N^4$-Ceroplastoyl Ara-C | 101 | 167 | 201 | | | |
| Control | Ara-C | 90 | 86 | 102 | 170 | (optimal dose 30 mg/Kg) | |

*Arabinofuranosylcytosine

The evaluation of the antitumor activity was represented in the above table by the survival rate T/C (%) which was the mean life time of the groups receiving an injection of the compound of this invention divided by the mean life time of the group which did not receive an injection of the compound of this invention multiplied by 100.

In the above table, a survival rate figure of 397 corresponds to the case where all of the mice survived.

From these results, it has been confirmed that the compounds of this invention are superior in antitumor activity to 1-β-D-arabinofuranosylcytosine.

While the invention has been described in detail and with reference to specific embodiments thereof, it will be apparent to one skilled in the art that various changes and modifications can be made therein without departing from the spirit and scope thereof.

What is claimed is:

1. An $N^4$-acyl-1-β-D-arabinofuranosylcytosine having the following formula:

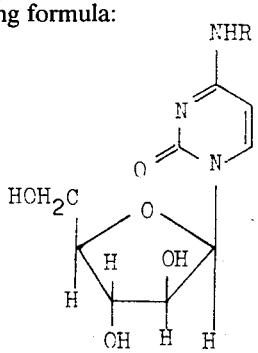

wherein R is an aliphatic acyl group having 14 to 35 carbon atoms.

2. The $N^4$-acyl-1-β-D-arabinofuranosylcytosine of claim 1 wherein said aliphatic acyl group is myristoyl, pentadecanoyl, palmitoyl, palmitoleoyl, vaccenoyl, margaroyl, stearoyl, oleoyl, elaidoyl, linoleoyl, linolenoyl, nonadecanoyl, arachidoyl, arachidonoyl, heneicosanoyl, behenoyl, tricosanoyl, pentacosanoyl, heptacosanoyl, nonacosanoyl, hentriacontanoyl or ceroplastoyl.

3. The $N^4$-acyl-1-β-D-arabinofuranosylcytosine of claim 1, wherein said aliphatic acyl group has 14 to 22 carbon atoms.

4. The $N^4$-acyl-1-β-D-arabinofuranosylcytosine of claim 3 wherein said aliphatic acyl group is myristoyl, pentadecanoyl, palmitoyl, palmitoleoyl, vaccenoyl, margaroyl, stearoyl, oleoyl elaidoyl, linoeoyl, linolenoyl, nonadecanoyl, arachidoyl, arachidonoyl, heneicosanoyl, or behenoyl.

5. The $N^4$-acyl-1-β-D-arabinofuranosylcytosine of claim 4, wherein said aliphatic acyl group is palmitoyl, margaroyl or stearoyl.

6. The $N^4$-acyl-1-β-D-arabinofuranosylcytosine of claim 5, wherein said aliphatic acyl group is margaroyl.

7. The $N^4$-acyl-1-β-D-arabinofuranosylcytosine of claim 5 wherein said aliphatic acyl group is stearoyl.

8. The $N^4$-acyl-1-β-D-arabinofuranosylcytosine of claim 3 wherein said aliphatic group has 19 to 22 carbon atoms.

* * * * *